United States Patent [19]

Ezure et al.

[11] Patent Number: 5,256,788
[45] Date of Patent: Oct. 26, 1993

[54] MORANOLINE DERIVATIVES AND THEIR PRODUCTION AND THE USE OF MORANOLINE AND ITS DERIVATIVES AS A STABILIZING AGENT FOR ENZYMES

[75] Inventors: Yohji Ezure, Otsu; Shigeaki Maruo, Ibaraki; Hiroshi Yamashita, Kyoto; Katsunori Miyazaki, Kyoto; Makoto Sugiyama, Kyoto, all of Japan

[73] Assignee: Nippon Shinyaku Co. Ltd., Japan

[21] Appl. No.: 475,158

[22] Filed: Feb. 5, 1990

[30] Foreign Application Priority Data

Feb. 13, 1989 [JP] Japan ................................. 1-33480
Feb. 13, 1989 [JP] Japan ................................. 1-33481

[51] Int. Cl.$^5$ .................................................. C07P 211/36
[52] U.S. Cl. ................................. 546/242; 536/4.1; 536/17.4; 536/18.6; 536/18.5; 536/46; 536/124; 435/96; 435/97; 435/101
[58] Field of Search .................... 435/101, 96, 97; 536/4.1; 546/242

[56] References Cited

PUBLICATIONS

Sugiyama et al., *Chemical Abstracts*, vol. 109(23), Dec. 5, 1988, #209662F.
Ezure et al., *Chemical Abstracts*, vol. 108(3), Jan. 18, 1988, #22213X.
Ezure et al., *Chemical Abstracts*, vol. 108(3), Jan. 18, 1988, #22214y.
Ezure et al., *Agric. Biol. Chem.*, vol. 53(1), Jan. 1989, pp. 61-68.

*Primary Examiner*—Ronald W. Griffin
*Assistant Examiner*—Pamela S. Webber
*Attorney, Agent, or Firm*—Rosenman & Colin

[57] ABSTRACT

The present invention relates to stabilizing agents for enzymes which comprises an enzyme stabilizing amount of an N-substituted moranoline derivative of the formula (III):

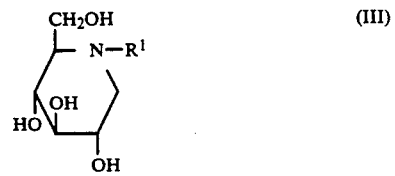

wherein $R^1$ is phenyl lower alkynyl, phenoxy lower alkenyl or phenoxy lower alkynyl, wherein the phenyl moiety is unsubstituted, or a glucose oligomer thereof.

6 Claims, 6 Drawing Sheets

MORANOLINE DERIVATIVES AND THEIR PRODUCTION AND THE USE OF MORANOLINE AND ITS DERIVATIVES AS A STABILIZING AGENT FOR ENZYMES

The present invention is concerned with a process for the production of an N-substituted moranoline derivative, to stabilizing agents for enzymes which comprises an enzyme stabilizing amount of an N-substituted moranoline derivative, to a method for stabilizing an enzyme utilizing an N-substituted moranoline derivative and to stabilized enzymes which contain an enzyme stabilizing amount of an N-substituted moranoline derivative.

More particularly, the present invention is concerned with an improvement in a process for producing an N-substituted moranoline derivative of the formula (I):

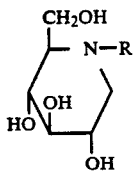
(I)

wherein R is hydrogen or lower alkyl, wherein the improvement comprises in sequence:

(a) using the culture broth obtained by culturing moranoline-producing bacteria as it is or subjecting the culture broth to alkylation;

(b) adding a glucose donor thereto and then reacting cyclodextrin glycosyl transferase (CGTase) to produce an oligo-glycosyl N-substituted moranoline derivative of the formula (II):

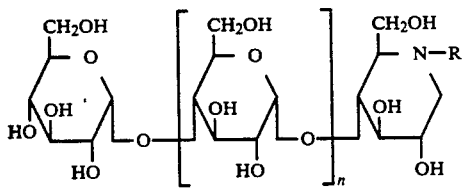
(II)

wherein R is as above defined and n is an integer from 0 to 24, and, if necessary, reacting glucoamylase (GA) to form a compound of the formula (II) wherein n is 0;

(c) isolating the compound of the formula (II) for example by fractionation or other suitable procedure; and (d) hydrolyzing the isolated compound of the formula (II) to obtain N-substituted moranoline derivative of the formula (I).

The present invention is also concerned with an improvement in a process for producing an N-substituted moranoline derivative of the formula (I):

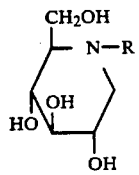
(I)

wherein R is hydrogen or lower alkyl, wherein the improvement comprises in sequence:

(a) using the culture broth obtained by culturing moranoline-producing bacteria as it is or subjecting the culture broth to alkylation;

(b) adding a glucose donor thereto and then reacting cyclodextrin glycosyl transferase (CGTase) to produce an oligo-glycosyl N-substituted moranoline derivative of the formula (II):

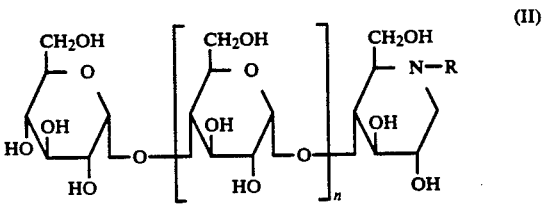
(II)

wherein R is as above defined and n is an integer from 0 to 24;

(c) reacting glucoamylase (GA) to form a glucosyl N-substituted moranoline derivative of the formula (II) wherein n is 0;

(d) isolating the glucosyl N-substituted moranoline derivative for example by fractionation or other suitable procedure; and (e) hydrolyzing the isolated glucosyl N-substituted moranoline derivative to obtain the N-substituted moranoline derivative of the formula (I).

A stabilizing agent for an enzyme is produced which comprises an enzyme stabilizing amount of an N-substituted moranoline derivative of the formula (III):

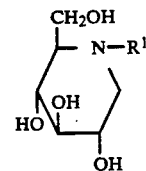
(III)

wherein $R^1$ is hydrogen, lower alkyl, phenyl lower alkyl, phenyl lower alkylenyl, phenyl lower alkynyl, phenoxy lower alkyl, phenoxy lower alkenyl or phenoxy lower alkynyl, wherein the phenyl moiety is unsubstituted or substituted, or a glucose oligomer thereof A method for stabilizing an enzyme which comprises reacting an enzyme on a substrate in the presence of an N-substituted moranoline derivative of the formula (III):

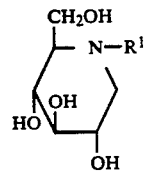
(III)

wherein $R^1$ is hydrogen, lower alkyl, phenyl lower alkyl, phenyl lower alkenyl, phenyl lower alkynyl, phenoxy lower alkyl, phenoxy lower alkenyl or phenoxy lower alkynyl, the phenyl moiety being unsubstituted or substituted, or a glucose oligomer thereof, wherein said substrate is said moranoline or is a different substrate.

A stabilized immobilized enzyme is produced which comprises said enzyme and a stabilizing amount of an N-substituted moranoline derivative of the formula (III):

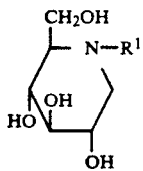

wherein $R^1$ is hydrogen, lower alkyl, phenyl lower alkyl, phenyl lower alkylenyl, phenyl lower alkynyl, phenoxy lower alkyl, phenoxy lower alkenyl or phenoxy lower alkynyl, wherein the phenyl moiety is unsubstituted or substituted, or a glucose oligomer thereof.

The phrase "an N-substituted moranoline" is intended to cover both the unsubstituted moranoline (R or $R^1$ is hydrogen) as well as the substituted moranolines.

The compound of the formula (I) wherein R is hydrogen was first extracted from a crude drug obtained from mulberry white bark and its utility as a drug was confirmed "Nippon Nogeikagaku kaishi" [50, 571, (1976)]. The compounds of the formula (I) wherein R is lower alkyl are known compounds described in, for example, Japanese Patent Publication No. 59-43459 (Patent No. 1268030), and are known to have pharmacological activity, for example, for preventing increase in blood sugar.

Thereafter, it was discovered that the compounds of the present invention had antiviral activity (Proc. Natl. Acad. Sci. USA, 9229P 1988).

According to the prior art, moranoline was produced by a process which comprises culturing a moranoline-producing bacteria (Japanese Patent Publication No. 56-099195).

The compounds of the formula (I) wherein R is lower alkyl could be readily obtained in a conventional manner, for example, by a process which comprises reacting moranoline with an appropriate alkylating agent (e.g., an alkyl halide), a process which comprises N-acylation followed by reduction to form an N-alkyl compound, a process which comprises reacting an alkyl aldehyde and a reducing agent.

Now, to apply the conventional processes described above, it was indispensable to obtain moranoline in a substantially pure form.

As a result of extensive investigations to obtain a strain having a high productivity of moranoline, many excellent results could be obtained and it has been discovered that in addition to the desired moranoline, a plurality of lower molecular basic water-soluble substances such as 1,5-dideoxy-1,5-imino-D-mannitol and 2-amino-2-deoxy-D-mannitol are contained in these culture broths capable of producing moranoline.

To obtain moranoline from the culture broth one can use an ion exchange method, activated charcoal adsorption method, fractionation through column chromatography with Sephadex, cellulose, silica gel, and the like to purify moranoline.

These methods enabled moranoline to be isolated, but a more efficient process is now desirable. Thus, to develop a process for isolating the desired moranoline from the culture broth has been an extremely important technical problem.

Therefore, an object of the present invention is to obtain the compounds of the formula (I) in a more efficient way.

As a result of extensive investigations to solve the technical problem, the present inventors have considered: (1) that sugar transfer reaction by cyclodextrin glycosyl transferase (CGTase) reacts with moranoline and N-lower alkylmoranoline but does not react with basic substances as impurities; (2) that glucose oligomers of the moranoline and N-substituted moranoline derivatives obtained by the reaction described above can be readily converted into glucosylmoranoline and glucosyl-N-lower alkylmoranolines by the process disclosed by the present inventors in Japanese Patent Publication No. 60-2038; (3) that the glucosylmoranoline and glucosyl-N-lower alkylmoranolines can readily be isolated by the process disclosed by the present inventors in Japanese Patent Application Laid-Open No. 62-242691; (4) that the glucosylmoranoline and glucosyl-N-lower alkylmoranolines can be converted into moranoline and N-lower alkylmoranolines by acid or glucoamylase (GA). By utilizing these processes, the desired compounds can be obtained from the culture broth in a high yield.

Furthermore, though it was very unexpected, during the course of their investigations, the present inventors have come across the fact that, in enzyme reactions upon sugar transfer of moranoline, by CGTase and upon leading glucose oligomers of moranoline, to glucosylmoranoline, by GA, the enzyme activity can be well stabilized by the presence of moranoline, as a substrate. This will be later described in more detail.

According to the present invention, moranoline-producing bacteria is first cultured. One useful bacteria is Actinomyces, and bacteria disclosed by the present inventors in Japanese Patent Publication No. 56-9919 can be used.

In the culture broth a plurality of lower molecular basic water-soluble substances such as 1,5-dideoxy-1,5-imino-D-mannitol, 2-amino-2-deoxy-D-mannitol, are contained, in addition to the desired moranoline, as described above.

When the N-lower alkylmoranolines are desired to be obtained as the final products, the culture broth is subjected to alkylation.

Examples of the lower alkyl moieties for R in the formulae (I) and (II) in accordance with the present invention include methyl, ethyl, n-propyl, i-propyl, n-butyl, i-butyl and tert-butyl.

According to one aspect of the present invention the alkylating agent is an alkyl halide. In such a case, N-lower alkyl 1,5-dideoxy-1,5-imino-D-mannitol and N-lower alkyl 2-amino-2-deoxy-D-mannitol, are contained as contaminants in the culture broth, in addition to N-lower alkylmoranolines.

In the present invention, glucose donors such as starch, dextrin and cyclodextrin are then added to the culture broth. Then, cyclodextrin glucosyl transferase (CGTase) is utilized to convert into glucose, oligomers of the formula (II):

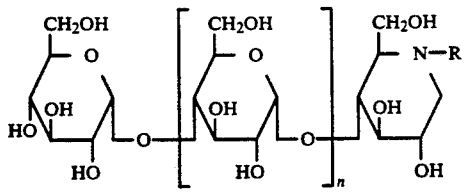

(II)

wherein R is as above defined and n is an integer from 0 to 24; and, if necessary, converted by glucoamylase (GA) into compounds (glucosyl compounds) of the formula (II) wherein n is 0.

It is best to react GA with the compound of the formula (II) wherein R is hydrogen. As will be later described, this is because the compound (glucosylmoranoline) of formula (II) wherein R is hydrogen and n is 0 has a specific property that the compound forms a molecular compound with methanol, whereby the resulting compound can be fractionally crystallized.

where it is unnecessary to react GA, the GA reaction may be omitted for purposes of increasing the yield or for convenience of operations.

During the course of the reaction, the contaminants 1,5-dideoxy-1,5-imino-D-mannitol, 2-amino-2-deoxy-D-mannitol and N-lower alkyl compounds thereof are not affected by the action of CGTase.

The reactions based on CGTase and GA are enzyme reactions. One of the important features of the present invention lies in establishing the means by which the enzyme reaction can be advantageously carried out.

According to the present invention, the compounds of the formula (II) can be very efficiently isolated by economical operations, for example, fractional crystallization, a compared to the compounds of the formula (I). Applicants utilize the physical and chemical properties whereby compound (II) is the glucose oligomer of compound (I).

For example, with respect to glucosylmoranoline, it forms a molecule compound with methanol by stirring in hydrated methanol so that crystallization is very efficient. Further with respect to N-lower alkylmoranoline, crystallization can be performed very efficiently likewise, using an arylsulfonic acid.

Further in the reaction, even after the compound (II) is recovered from the mother liquor, the residue can be re-used as the raw material by repeating the same procedure so that unrecovered compound (II) can be readily recovered. Therefore, the final recovery rate can be enhanced.

Thus, one object of the present invention lies in efficient isolation from the mixture and to increase the yield for isolation.

For the isolation described above, one may use the method described in Japanese Patent Application Laid-Open No. 61-115093 invented by the present inventors.

Compounds of the formula (II) obtained as described above can be further degraded into moranoline or N-lower alkylmoranolines and glucose through hydrolysis by heating in an acidic aqueous solution, e.g., hydrochloric acid aqueous solution or by reacting an excess of GA.

Glucose is a neutral substance and the product is a basic substance. Therefore, by treatment, e.g., by subjecting to strongly acidic ion exchange resin in a conventional manner, the product alone can be obtained. In performing the process, processes disclosed in Japanese Patent Application Laid-Open Nos. 62-242691 and 64-242692 filed by the present inventors are applicable.

In the case where the final product is used to produce other compounds, it is not always necessary to crystallize it. After the compound (II) is hydrolyzed, the product has a purity substantially sufficient to be used for synthetic reactions so that the product can be used for the synthetic reactions as it is without purification.

Technical progress on technology of enzyme reactions is remarkable in recent years. In particular, the immobilized enzyme method utilizing chitosan beads is much more effective than the known methods, for example, enzyme reaction in a solution, etc. in that an amount of enzyme used can be minimized and efficient reaction can be performed.

A plurality of patent applications were filed on the immobilized enzyme method utilizing chitosan beads. For example, in Japanese Patent Application Laid-Open No. 63-196290, there is disclosed a technique which comprises immobilizing cyclodextrin glucanotransferase onto porous chitosan beads and further crosslinking using a crosslinking agent.

The immobilized enzyme method can be applied also to the present invention.

Illustrating the process for preparing the immobilized enzyme applied to the present invention, a crosslinking agent is first reacted with chitosan beads to form crosslinking with the amino groups on the surface of chitosan beads. Thereafter, the enzyme in accordance with the present invention is immobilized onto the crosslinking agent at the end thereof.

A suitable crosslinking agent in accordance with the present invention, is for example, glutaraldehyde.

As the chitosan beads in accordance with the present invention, there may be used, for example, CHITO-PEARL (manufactured by Fujibo Co., Ltd.), BCW-1000 Series, etc. To produce the immobilized enzyme in accordance with the present invention, the chitosan beads described above are added to a suitable buffer solution (e.g., 0.1M acetate buffer solution showing pH of 6.0) at a suitable temperature (e.g., room temperature). The mixture is gently shaken and glutaraldehyde having a suitable concentration (e.g., 25 w/v%) is added thereto. After gently shaking for a suitable time period (e.g., 1 to 48 hours), the mixture is filtered and then washed with water. Then a CGTase solution having a suitable concentration (e.g., 1 to 500 mg/ml) in a suitable buffer solution (e.g., 0.025M acetate buffer solution having a pH of 6.0) is added. After gently shaking for a suitable period of time (e.g., 1 to 48 hours), the solution is filtered and washing with water, giving the immobilized enzyme.

The process described above was first established by the present inventors. According to this process, the immobilized enzyme method can be performed without using the technique disclosed in Japanese Patent Application Laid-Open No. 63-196290 described above.

During the course of accomplishing the present invention, the present inventors have found surprisingly that when the moranoline or N-substituted moranoline derivatives in accordance with the present invention or glucose oligomers thereof are present in the aforesaid enzyme reactions in accordance with the present invention, the enzyme is stabilized and the enzyme activity is not reduced even after a prolonged period of time.

For example, in immobilized CGTase, more than 90% of the initial activity can be maintained even after 366 days at 55° C. In the case of immobilized GA, more than 80% of the initial activity was maintained after 43 days at 55° C., more than 80% after 175 days at 50° C. and more than 90% after 133 days at 40° C.

Thus, the immobilized enzyme is extremely well stabilized.

The present invention also includes a method for stabilizing enzymes such as cyclodextrin glycosyl transferase (CGTase), glucoamylase (GA), β-glucosidase (GD), α-amylase, β-amylase, malto-oligosaccharide-forming enzyme and the like.

CGTase is an enzyme generally used for producing cyclodextrin from starch on an industrial scale. Cyclodextrin is a substance widely used for various foodstuffs as a thickener. Cyclodextrin is also a substance which is essential for preparing clathrate compounds having wide applications to improved stability of drugs or deodoration of smelly substances. Accordingly, stabilizing CGTase is a highly important and significant advance in the art.

GA is an enzyme conventionally used for preparing glucose from starch. Stabilization of GA also represents a highly important and significant advance in the art.

The other enzymes stabilized in accordance with the present invention are substances which are essential for manufacturing drugs or providing inexpensive foodstuffs of high quality and are very often utilized. To stabilize these enzymes is a highly important and significant advance in the art.

It has been recognized in the art that in particular, the immobilized enzyme method utilizing chitosan beads is much more effective than the previously known methods, for example, enzyme reaction in a solution, in that an amount of enzyme used can be minimized and efficient reaction can be performed.

A plurality of patent applications were filed on the immobilized enzyme method utilizing chitosan beads. For example, in Japanese Patent Application Laid-Open No. 63-196290, there is disclosed a technique which comprises immobilizing cyclodextrin glucanotransferase onto porous chitosan beads and further crosslinking using a crosslinking agent.

Many investigations were made on efficient application of the enzyme described above but satisfactory results were not consistently obtained with respect to stabilization of the enzyme itself. Moreover, the activity of the enzyme was lost with the passage of time. For example, in the case of CGTase, in general, the activity is reduced to half in several days and after ten days, the activity is completely lost.

In such a case, even though it is an immobilized enzyme, there was no way to provide active enzyme other than freshly supplying the enzyme itself. One of the technical difficulties that the present invention attempts to overcome lies in this point.

As a result of extensive investigations to solve the technical problem, the present inventors have discovered that the problem described above can be skillfully solved by reacting an enzyme in the presence of an N-substituted moranoline derivative of the formula (III):

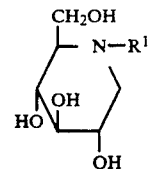

wherein R is hydrogen, lower alkyl, phenyl lower alkyl, phenyl lower alkenyl, phenyl lower alkynyl, phenoxy lower alkyl, phenoxy lower alkenyl or phenoxy lower alkynyl, wherein the phenyl moiety is unsubstituted or substituted, or a glucose oligomer thereof, wherein said substrate is said N-substituted moranoline derivative or is a different substrate.

The present inventors have also found that the enzyme after having been reacted in the presence of a compound of the formula (III) described above still maintains its highly activated level of activity after removal from or separation from said compound.

Accordingly, one of the characteristics of the present invention lies in the method for stabilizing an enzyme by performing an enzyme reaction in the presence of a compound of the formula (III) or a glucose oligomers thereof. Another characteristic of the present invention lies in the fact that the enzyme per se is stabilized by performing the enzyme reaction in the presence of a compound of the formula (III) or a glucose oligomers thereof.

Illustrating the process for preparing the immobilized enzyme of the present invention, a crosslinking agent is firstly reacted with chitosan beads to form crosslinking with the amino groups on the surface of chitosan beads. Thereafter, in accordance with the present invention the enzyme is immobilized onto the crosslinking agent at the end thereof.

As the crosslinking agent in accordance with the present invention, glutaraldehyde may be used.

As the chitosan beads in accordance with the present invention, there may be used, for example, CHITOPEARL (manufactured by Fujibo Co., Ltd.), BCW-1000 Series, etc.

To produce the immobilized enzyme in accordance with the present invention, the chitosan beads described above are added to a suitable buffer solution (e.g., 0.1M acetate buffer solution showing pH of 6.0) at a suitable temperature (e.g., room temperature). The mixture is gently shaken and glutaraldehyde having a suitable concentration (e.g., 25 w/v%) is added thereto. After gently shaking the mixture for a suitable time period (e.g., 1 to 48 hours), it is filtered and then washed with water. Then a CGTase solution having a suitable concentration (e.g., 1 to 500 mg/ml) in a suitable buffer solution (e.g., 0.025M acetate buffer solution showing pH of 6.0) is added. After gently shaking for a suitable period of time (e.g., 1 to 48 hours), the solution is filtered and washed with water to give the immobilized enzyme.

The process described above has been first established by the present inventors. According to this process, the immobilized enzyme method can be performed without using the technique disclosed in Japanese Patent Application Laid-Open No. 63-196290 described above.

For example, in immobilized CGTase, more than 90% of the initial activity can be maintained even after 413 days passed at 55° C. In the case of immobilized GA, more than 80% of the initial activity was maintained after 43 days passed at 55° C., more than 80% after 175 days at 50° C., more than 90% after 133 days at 40° C.

While the mechanism is not exactly clear, it is assumed that some function would be exhibited in association with enzyme, since compounds of the formula (III) are pseudosugars (pseudopiperidinose) having a structure similar to glucose which is a constituent sugar of these enzyme substrate (for example, starch, dextrin, malto-oligosaccharide, maltose).

The enzyme in this case may be any of dissolved state or immobilized state but for industrial purposes, immobilized enzyme is generally used.

The compounds in accordance with the present invention which are represented by (I) are known substances and can be obtained by processes disclosed in, for example, Japanese Patent Publication Nos. 56-099195, 60-2038, 61-2076, 62-242691, etc.

The glucose oligomer in accordance with the present invention is of the formula (IV):

$$\text{(IV)}$$

wherein $R^1$ is as above defined; and n is an integer from 0 to 24.

Examples of lower alkyl for $R^1$ include methyl, ethyl, n-propyl, isopropyl, n-butyl, isobutyl, sec-butyl and tert-butyl.

Preferably the number of carbon atoms in the alkyl moiety in phenylalkyl is 1 to 5. The phenyl moiety includes both substituted and unsubstituted.

Preferably the number of carbon atoms in the alkenyl moiety in phenylalkenyl is 2 to 5. The phenyl moiety includes both substituted and unsubstituted.

Preferably the number of carbon atoms in the alkynyl moiety in phenylalkynyl is 2 to 5. The phenyl moiety includes both substituted and unsubstituted.

Preferably the number of carbon atoms in the alkyl moiety in phenoxyalkyl is 1 to 5. The phenyl moiety includes both substituted and unsubstituted.

Preferably the number of carbon atoms in the alkenyl moiety in phenoxyalkenyl is 2 to 5. The phenyl moiety includes both substituted and unsubstituted.

Preferably the number of carbon atoms in the alkynyl moiety in phenoxyalkynyl is 2 to 5. The phenyl moiety includes both substituted and unsubstituted.

The stabilization of the enzyme in accordance with the present invention can be performed as follows.

In stabilization of the immobilized enzyme, a compound of the present invention of the formula (III) is added to the immobilized enzyme obtained as described above. When the compound of the present invention is used as a substrate, the stabilization according to the present invention can be effected simply by adding the substrate per se. When the substrate is not the compound of the present invention, the enzyme reaction can be carried out with respect to the immobilized enzyme by stabilizing it with a compound of the present invention.

After the compound of the present invention is added, the reaction is carried out at a temperature conventional for ordinary enzyme reaction for a time period for ordinary enzyme reaction.

The following non-limitative examples more particularly illustrate the present invention.

Reference Example 1

Immobilization of CGTase (1)

After 10 l of CHITOPEARL BCW-3010 manufactured by Fujibo Co., Ltd. was immersion-treated in 40 l of 0.1M acetate buffer solution (pH 6.0) containing 2.5 w/v% glutaraldehyde at room temperature for 24 hours, the mixture was thoroughly washed with ion exchange water. Then, CGTase [manufactured by Hayashibara Biochemical Research Institute, derived from *Bacillus stearothermophilus*] corresponding to 20 mg of protein was added per 1 ml of CHITOPEARL and acetate buffer solution (pH 6.0) was further added to the mixture in a final concentration of 0.025M to make the whole volume 30 l. The system was immersed at room temperature for 24 hours as it was. Thereafter, the mixture was thoroughly washed with deionized water to give immobilized CGTase. A protein adsorption amount of the resulting beads was 19.5 mg/ml (bead).

Reference Example 2

Immobilization of CGTase (2)

CGTase derived from *Bacillus stearothermophilus* was immobilized in a manner similar to Reference Example 1 to give a protein adsorption amount of 5 mg/ml (bead).

Reference Example 3

Immobilization of GA

After glucozyme NL-3 manufactured by Amano Pharmaceutical Co., Ltd. was dialyzed, it was adjusted to a protein concentration of 60 to 65 mg/ml. This was used as GA aqueous solution.

After 1 l of CHITOPEARL BCW-3010 manufactured by Fujibo Co., Ltd. was immersion-treated in 3 l of 50 mM acetate buffer solution (pH 5.0) containing 2.5 w/v% glutaraldehyde at room temperature for 24 hours, the mixture was thoroughly washed with deionized water. Then, GA aqueous solution corresponding to 100 mg of protein was added per 1 ml of CHITOPEARL and water was further added to the mixture to make the whole volume 3 l. The system was immersed at room temperature for 24 hours as it was. Thereafter, the mixture was thoroughly washed with deionized water to give immobilized GA. A protein adsorption amount of the resulting beads was 12.8 mg/ml (bead).

Reference Example 4

Stabilization of immobilized CGTase (in sugar transfer reaction solution of moranoline)

The immobilized CGTase, 10 ml, obtained in Reference Example 1 was added to 100 ml of aqueous solution with the pH being not adjusted containing 2.5 w/v% of moranoline and 25 w/v% of Amicol No. 6L [manufactured by Nichiden Chemical Co., Ltd.] followed by rotary shaking at 55° C. Thereafter, beads formed and (after a definite period of time as illustrated below) the beads (immobilized CGTase) were filtered through a glass filter. After thoroughly washing with water, the enzyme activity of the immobilized CGTase was determined as follows.

(Method for determination of enzyme activity of immobilized CGTase)

The beads (washed immobilized CGTase after a definite period of time at 55° C.), 1 ml, was added to 10 ml of aqueous solution with the pH being not adjusted containing 2.5 w/v% of moranoline and 25 w/v% of Amicol No. 6L followed by reacting at 55° C. for 24 hours. The reaction solution 3 ml, was passed through 7 ml of strongly acidic ion exchange resin DOWEX 50W×2 (H ). After thoroughly washing with water, elution was performed with 0.5N ammonia water. The eluate was concentrated to dryness under reduced pressure and the residue was dissolved in 3 ml of water. 10 μl of the solution was applied to and analyzed by high performance liquid chromatography to determine a concentration of the unreacted moranoline. The analytical conditions for high performance liquid chromatography were as follows: column (Nucleosil 5NH$_2$, 5 μm, 4 mm i.d.×25 cm), developing solvent acetonitrile-water=70:30), detector (Hitachi 655A-30, RI detector), data processor (Hitachi D-2000).

$$\text{Reaction progress rate (\%)} = \frac{25 - [\text{unreacted moranoline (mg/ml)}] \times 100}{25}$$

Where the reaction progress rate was made 100 when rotary shaking started at 55° C., a relative reaction progress rate after a definite period of time passed was calculated according to the above equation. The thus obtained value was made an enzyme activity retention rate. The results are shown in Table 1. The fact that the enzyme activity of the immobilized CGTase was stabilized by the moranoline in accordance with the present invention is clearly shown.

TABLE 1

| Time passed (day) | 0 | | 14 | 21 | 28 | | |
|---|---|---|---|---|---|---|---|
| Activity retention rate (%) | 100 | | 100 | 102.7 | 101.9 | | |
| day | 37 | 53 | 65 | 78 | 93 | 100 | |
| % | 100.8 | 102.3 | 104.3 | 100.7 | 99.7 | 100.5 | |
| day | 119 | 140 | 163 | 178 | 198 | 210 | |
| % | 97.0 | 100.3 | 99.3 | 98.4 | 92.5 | 95.6 | |
| day | 231 | 246 | 262 | 274 | 288 | 302 | 322 |
| % | 92.5 | 93.0 | 92.3 | 92.5 | 91.7 | 92.0 | 92.7 |
| day | 339 | 353 | 366 | | | | |
| % | 91.5 | 93.9 | 90.0 | | | | |

Reference Example 5

Stabilization of immobilized CGTase (sugar transfer continuous reaction of N-methylmoranoline)

The immobilized CGTase, 20 ml, obtained in Reference Example 1 was packed in a column having a diameter of 1 cm equipped with a jacket and a solution with the pH being not adjusted containing 1.5 w/v% of N-methylmoranoline and 9 w/v% of soluble starch was continuously passed through the column at 55° C. in a passing velocity of 160 ml/day to react them, whereby the reaction progress rate of the passing liquid was determined with passage of time. The reaction progress rate and activity retention rate were determined in a manner similar to Reference 4. The results reveal that even after 140 days, almost 100% of the activity was retained.

Reference Example 6

Stabilization of immobilized CGTase (moranoline, moranoline glucose oligomer)

To 1 ml of the immobilized CGTase obtained in Reference Example 2 were added moranoline (2.5 w/v%) and moranoline glucose oligomer (mixture) (5.0 w/v%) to make whole volume 10 ml. The mixture was shaken at 55° C. The glucose oligomer of moranoline refers to a basic fraction obtained by treating the sugar transfer reaction solution obtained in Example 7 with strongly acidic ion exchange resin DOWEX 50W×2 (H$^+$), thoroughly washing with water, eluting with 0.5N ammonia water and concentrating the eluate to dryness.

When the enzyme activity in adjustment was made 100, the residual enzyme activity retention rate (%) is shown in Table 2. Determination of the enzyme activity, etc. were all the same as in Reference Example 4.

It is clear that moranoline and the glucose oligomer of moranoline have the action of retaining the activity of CGTase.

TABLE 2

| | 14 Days | 28 Days | 42 Days |
|---|---|---|---|
| None | 17.7% | 12.5% | 0.0% |
| Moranoline | 81.6 | 77.8 | 70.8 |
| Glucose oligomer of moranoline | 100.0 | 99.0 | 95.7 |

Reference Example 7

Stabilization of immobilized CGTase (N-substituted moranoline, N-substituted glucosylmoranoline)

To 1 ml of the immobilized CGTase obtained in Reference Example 1 were added N-substituted moranoline (0.5 w/v% and N-substituted glucosylmoranoline (0.5 w/v%) to make whole volume 10 ml. After the mixture was shaken at 55° C. for 14 days, the residual enzyme activity was measured. The residual enzyme activity rate when the initial enzyme activity was made 100 is shown in Table 3. Determination of the enzyme activity was performed as in Reference Example 4.

It is clear that the compound of the present invention is quite well stabilized.

TABLE 3

| Residual enzyme activity rate (%) | |
|---|---|
| | Activity Rate (%) |
| Water | 15.0% |
| N-Butylmoranoline | 68.5 |
| N-Phenylethylmoranoline | 75.0 |
| N-Phenoxyethylmoranoline | 37.1 |
| Glucosyl-N-butylmoranoline | 100.0 |
| Glucosyl-N-phenylethylmoranoline | 88.4 |
| Glucosyl-N-phenoxyethylmoranoline | 74.0 |

Reference Example 8

Stabilization of immobilized GA (sugar transfer reaction liquid of moranoline)

The pH of the reaction solution containing the unreacted moranoline, the unreacted Amicol No. 6L and oligoglucosylmoranoline prepared by the process of Example 7 was adjusted to pH 5.2 using sulfuric acid. The reaction solution was continuously passed at 50° C. through a column having a diameter of 1 cm equipped with a jacket, which had been packed with 20 ml of the immobilized GA obtained in Reference Example 3, in a passing velocity of 480 ml/day to react them. After reacting for a definite period of time, the immobilized GA in the column was taken out and the enzyme activity was determined by the following method, whereby the activity retention rate (stability) when the enzyme activity at the initiation of the reaction was made 100% was determined. The results are shown in Table 4.

Method for determination of enzyme activity of immobilized GA

A definite amount (wet weight, 30 to 80 mg) of the immobilized GA was taken on a glass filter and gently sucked to filter the water off. Thereafter the immobilized GA on the glass filter was put on a lens paper to remove an excess of water. Then, the residue was charged in a sample bottle with a stopper to determine wet weight of the immobilized GA. Next, the immobilized GA was added to 10 ml of 5% maltose solution (0.05M acetate buffer solution, pH 4.6) followed by incubation at 37° C. for 20 minutes. 100 μl of the reaction solution was added to 0.05N sodium hydroxide to terminate the reaction.

Using 10 μl of the reaction terminated solution, glucose was quantitatively determined. The quantitative determination of glucose was performed using DIA COLOR GC (manufactured by Ono Pharmaceutical Co., Ltd.).

The activity was defined as follows. The activity of an enzyme which produces 1 μM of glucose for one minute is made one unit. For blank, 0.05N sodium hydroxide mixed with substrate in an equimolar volume instead of the reaction solution was used.

In this case, the activity of the immobilized GA showed $5.56 \times OD_{SA}/OD_{STD}$/wet weight of the immobilized GA, wherein $OD_{SA}$ represents absorbency of sample (immobilized GA) at 500 nm and $OD_{STD}$ represents absorbency of 1 mg/ml glucose aqueous solution at 500 nm. In Table 4, the value of the activity retention rate varies but this is due to error in measurement. The stabilizing action of the compound of the present invention to the immobilized GA is clearly shown.

TABLE 4

| Time passed (day) |     |     |     |     | 0   | 7   | 14  | 21  | 28  |
|---|---|---|---|---|---|---|---|---|---|
| Activity retention rate (%) |     |     |     |     | 100 | 96  | 82  | 88  | 80  |
| day | 35  | 42  | 49  | 56  | 63  | 70  |     |     |     |
| %   | 92  | 85  | 104 | 111 | 96  | 97  |     |     |     |
| day | 77  | 84  | 91  | 98  | 105 | 112 |     |     |     |
| %   | 90  | 79  | 86  | 82  | 75  | 76  |     |     |     |
| day | 119 | 126 | 133 | 140 | 147 | 154 |     |     |     |
| %   | 76  | 76  | 79  | 76  | 86  | 75  |     |     |     |
| day | 161 | 168 | 175 |     |     |     |     |     |     |
| %   | 77  | 77  | 80  |     |     |     |     |     |     |

Reference Example 9

Stabilization of immobilized GA (sugar transfer reaction liquid of moranoline)

In a manner similar to Reference Example 8, the experiment was performed at 40° C. The results are shown in Table 5.

TABLE 5

| Time passed (day) |     |     |     |     | 0   | 7   | 14  | 21  | 28  |
|---|---|---|---|---|---|---|---|---|---|
| Activity retention rate (%) |     |     |     |     | 100 | 96  | 86  | 92  | 77  |
| day | 35  | 42  | 49  | 56  | 63  | 70  |     |     |     |
| %   | 96  | 96  | 127 | 130 | 108 | 97  |     |     |     |
| day | 77  | 84  | 91  | 98  | 105 | 112 |     |     |     |
| %   | 90  | 86  | 107 | 89  | 86  | 83  |     |     |     |
| day | 119 | 126 | 133 | 140 | 147 | 154 |     |     |     |
| %   | 90  | 97  | 89  | 92  | 96  | 96  |     |     |     |
| day | 161 | 168 | 175 |     |     |     |     |     |     |

TABLE 5-continued

| % | 97 | 83 | 90 |
|---|---|---|---|

Reference Example 10

Stabilization of GA (aqueous solution) (moranoline, N-methylmoranoline)

Since moranoline and N-methylmoranoline inhibit the enzyme activity of glucoamylase, the stabilizing effect to glucoamylase in a solution state was examined as follows. As the enzyme, Rhizopus niveus-derived reagent glucoamylase manufactured by Seikagaku Kogyo Co., Ltd. was used.

After 5 mg of the enzyme was dissolved in 1 ml of 0.1M acetate buffer solution (pH 5.0), moranoline and N-methylmoranoline were dissolved in the solution in a concentration of 6000 μg/ml. The solution was charged in a test tube with a screw stopper followed by incubation at 50° C. Each enzyme solution was diluted with 0.1M acetate buffer solution (pH 5.0) to 100-fold and 100 μl of the dilution was taken. After 400 μl of 5% maltose solution (0.05M acetate buffer solution, pH 4.6) was added thereto, the mixture was reacted at 40° C. for 20 minutes. 100 μl of the reaction solution was taken and 100 μl of 0.05N sodium hydroxide was added thereto to terminate the reaction. Further 100 μl of the reaction solution was taken and 3.0 ml of reagent DIA COLOR GC for measuring glucose was added thereto. The mixture was settled at 37° C. for 30 minutes to form a color. Thereafter, the system was ice cooled and absorbency was measured at 500 nm to determine the glucose amount. The amount of glucose produced was made enzyme activity in the co-presence of inhibitor. When the initial enzyme activity (amount of glucose produced) was made 10, relative enzyme activity was determined. The results are shown in FIG. 1. The enzyme stabilizing activity of the compound of the present invention is clearly demonstrated.

Example 1

Culture of moranoline-producing bacteria

In an Erlenmeyer flask of 500 ml volume was charged 200 ml of medium having a composition of 2% starch, 1% soybean powders, 0.05% potassium chloride, 0.05% magnesium sulfate heptahydrate, 0.2% sodium chloride and 0.35% calcium carbonate (pH 7.2). After sterilization in a conventional manner, several platinum loops of spores from the slant culture of Streptomyces lavendulae SEN-158 strain were inoculated on the medium and shake cultured at 27° C. for 3 days at 200 r.p.m. The resulting culture was used as a seed culture solution.

In a jar fermenter of 420 l was charged 250 l of medium having a composition of 8% starch, 3% soybean powders, 1.5% yeast extract, 0.05% potassium chloride, 0.05% magnesium sulfate heptahydrate, 0.1% sodium chloride and 0.15% calcium carbonate (pH 7.2). After sterilization in a conventional manner, 2.4 l of the seed culture broth was inoculated on the medium followed by culturing at 27° C. for 10 days at 100 r.p.m. in an aerial amount of 125 /min. In a manner similar to Reference Example 4, moranoline in the culture broth was quantitatively determined by high performance liquid chromatography. As the result, about 3500 μg/ml of moranoline was obtained.

Example 2

Partial purification of moranoline-containing culture broth (1)

The culture broth obtained by the process of Example 1 was applied to a ultrafiltration membrane (UF Module; MU-6303-HG; made by Kuraray Co., Ltd.). The passed liquid was further applied to a reverse osmosis membrane (HR-5155 F1; hollow fiber type; manufactured by Toyobo Co., Ltd.) and concentrated. The liquid which had not passed was made the partially purified product.

Example 3

Partial purification of moranoline-containing culture broth (2)

The culture broth obtained by the process of Example 1 was filtered through a press filter. The resulting culture filtrate was subjected to a column packed with 70 l of strongly acidic ion exchange resin DIA ION SK-104 (H+). After thoroughly washing with water, the column was eluted with 1N ammonia water.

After the eluate was concentrated under reduced pressure, the concentrate was passed through a column packed with 35 l of strongly basic ion exchange resin DIA ION SA-11A (OH−) followed by elution with water. After the eluate was concentrated under reduced pressure, the concentrate was made the partially purified product.

Example 4

N-methylation of moranoline-containing culture broth

To 1000 ml of the culture broth obtained in Example 1 was added 100 g of high flow super cell. The mixture was filtered to give 850 ml of the culture filtrate. After 30 ml of formalin and about 15 ml of commercially available Raney nickel for industrial use were added to the culture filtrate, catalytic hydrogenation was carried out at norma temperature under normal pressure.

After completion of the reaction, the catalyst was filtered off and the filtrate was passed through a column packed with 500 ml of strongly acidic ion exchange resin DOWEX 50W x 2 (H+). After thoroughly washing with water, the column was eluted with 1N ammonia water. Thus, the partially purified culture solution containing N-methylmoranoline which could be used for the subsequent reaction was obtained.

Example 5

N-(n-butylation) of moranoline-containing culture broth (1)

To 200 ml of the culture broth obtained in Example 1 was added 100 g of high flow super cell. The mixture was filtered to give 1800 ml of the culture filtrate. After the culture filtrate was concentrated to dryness under reduced pressure, 200 ml of N, N-dimethylformamide was added. After stirring, the mixture was filtered and the filtrate was washed further with 100 ml of N,N-dimethylformamide. The filtrate and the washing liquid were combined and 16.1 g of n-butyl bromide and 21.8 g of potassium carbonate were added thereto. The mixture was reacted at 110° C. for 7 hours.

After completion of the reaction, filtration was conducted and the solvent was removed under reduced pressure to give the partially purified, N-(n-butylated) product of the culture solution usable for the subsequent reaction.

Example 6

N-(n-butylation) of moranoline-containing culture broth (2)

The partially purified product treated as in Example 3 obtained by treating 1000 ml of the culture broth obtained in Example 1 was concentrated to dryness under reduced pressure. Under ice cooling, 50 ml of methanol was added to the residue After stirring, 20.5 ml of n-butyl aldehyde, 12.0 ml of 5% hydrochloric acid-methanol solution and 2.5 g of sodium cyanoborohydride were added to the mixture. After stirring for 30 minutes, the mixture was reacted at room temperature for 16 hours.

The solvent was removed under reduced pressure and the residue was dissolved in 25 ml of water followed by distributing 3 times with 15 ml of chloroform. The aqueous phase was passed through a column packed with 100 ml of strongly acidic ion exchange resin DIA ION SK-104 (H+). After thoroughly washing with water, the column was eluted with 0.5N ammonia water. The eluate was concentrated under reduced pressure to give the partially purified, N-(n-butylated) product of the culture solution usable for the subsequent reaction.

Example 7

Sugar transfer reaction of the partially purified product of moranoline-containing culture broth (1)

The partially purified product (150 l; containing about 7 kg of moranoline) obtained in a manner similar to Example 1 by treating the culture broth (2000 ) cultured in a manner similar to Example 2 was charged in the jar fermenter in a reaction apparatus comprising a jar fermenter of 420 l volume having connected therewith a column of 50 l volume. Furthermore, 70 kg of Amicol No. 6L was added to the mixture and heated to dissolve the same. After pH was adjusted to 9.0 with 6N sodium hydroxide, water was added to make the whole volume 280 l. After 30 of the immobilized CGTase prepared by the process of Reference Example 1 was packed in the column, the reaction was carried out at 55° C. for 48 hours while circulating at a flow rate of 3 l/min to give the sugar transfer reaction liquid of moranoline.

Example 8

Sugar transfer reaction of the partially purified product of moranoline-containing culture broth (2)

The partially purified product (100 l; containing about 7 kg of moranoline) obtained by treating in a manner similar to Example 3 the culture solution (2000 l) cultured in a manner similar to Example 1 was charged in the jar fermenter in a reaction apparatus comprising a jar fermenter of 420 l volume having connected therewith a column of 50 l volume. Furthermore, 70 kg of Amicol No. 6L was added to the mixture and heated to dissolve the same. In such a state that pH was not adjusted, water was added to make the whole volume 300 l. After 30 l of the immobilized CGTase prepared by the process of Reference Example 1 was packed in the column, the reaction was carried out at 55° C. for 72 hours while circulating at a flow rate of 3 l/min to give the sugar transfer reaction liquid of moranoline.

Example 9

Sugar transfer reaction of N-methylmoranoline-containing culture broth

After 12 g of soluble starch was dissolved in the culture broth containing N-methylmoranoline (50 ml; containing about 3 g of N-methylmoranoline) prepared by the process of Example 4 with heating, water was added to make the whole volume 100 ml. Then 10 ml of immobilized CGTase prepared by the process of Reference Example 1 was added to the solution. After reacting at 55.C for 48 hours, the reaction mixture was filtered through a glass filter to give the sugar transfer reaction solution of N-methylmoranoline.

Example 10

Sugar transfer reaction or N (n-butyl)moranoline-containing culture broth (1)

After a part of the partially purified product of the N-(n-butyl)moranoline-containing culture broth prepared by the process of Example 5 [18.3 g; among them about 4.0 g was N-(n-butyl)moranoline] was dissolved in 100 ml of water and 30 g of Amicol No. 6L was dissolved in the solution with heating. Water was added to make the whole volume 200 ml.

Then 10 ml of immobilized CGTase prepared by the process of Reference Example 2 was added to the solution. After reacting at 55° C. for 48 hours, the reaction mixture was filtered through a glass filter to give the sugar transfer reaction solution of N-(n-butyl)moranoline.

Example 11

Sugar transfer reaction of N-(n-butyl)moranoline-containing culture broth (2)

After a part of the partially purified product of the N-(n-butyl)moranoline-containing culture broth prepared by the process of Example 6 [10.0 g; among them about 8.0 g was N-(n-butyl)moranoline] was dissolved in 80 ml of water and λ g of Amicol No. 6L was dissolved in the solution with heating. Water was added to make the whole volume 160 ml.

Then 20 ml of immobilized CGTase prepared by the process of Reference Example 1 was added to the solution. After reacting at 55° C. for 48 hours, the reaction mixture was filtered through a glass filter to give the sugar transfer reaction solution of N-(n-butyl)moranoline.

Example 12

GA reaction in accordance with Example 7 (moranoline)

In a reaction apparatus composed of a jar fermenter of 420 l volume connected with a column of 50 l volume, of the immobilized GA prepared by the process of Reference Example 3 was packed in the column of volume and 280 l of the moranoline sugar transfer reaction solution (sugar transfer reaction solution obtained by reacting about 7 kg of moranoline) prepared by the process of Example 7 was charged in the jar fermenter. After pH was adjusted to 5.2 with conc. sulfuric acid, the reaction was carried out at 50° C. for 19 hours while circulating them at a flow rate of 3 l/min.

Example 13

GA reaction in accordance with Example 8 (moranoline)

In a reaction apparatus composed of a jar fermenter of 420 l volume connected with a column of 50 l volume, 15 l of the immobilized GA prepared by the process of Reference Example 3 was packed in the column of 50 l volume and 300 l of the moranoline sugar transfer reaction solution (sugar transfer reaction solution obtained by reacting about 7 kg of moranoline) prepared by the process of Example 8 was charged in the jar fermenter. After pH was adjusted to 5.2 with conc. sulfuric acid, the reaction was carried out at 40° C. for 18 hours while circulating them at a flow rate of 3 l/min.

Example 14

GA reaction in accordance with Example 9 (N-methylmoranoline)

After conc. sulfuric acid was added to 100 ml of the N-methylmoranoline sugar transfer reaction solution (containing about 3 g of N-methylmoranoline prior to the sugar transfer reaction) prepared by the process of Example 9 to adjust pH to 5.2, 10 ml of the immobilized GA prepared by the process of Reference Example 3 was added to the mixture followed by reacting at 50° C. for 20 hours. The reaction mixture was filtered through a glass filter to remove the immobilized GA to give the GA reaction solution.

Example 15

GA reaction in accordance with Example 10 (N-(n-butyl)moranoline)

After conc. sulfuric acid was added to 200 ml of the N-(n-butyl)moranoline sugar transfer reaction solution (containing about 3 g of N-(n-butyl)moranoline prior to the sugar transfer reaction) prepared by the process of Example 10 to adjust pH to 5.2, 20 ml of the immobilized GA prepared by the process of Reference Example 3 was added to the mixture followed by reacting at 50° C. for 20 hours. The reaction mixture was filtered through a glass filter to remove the immobilized GA to give the GA reaction solution

Example 16

GA reaction in accordance with Example 11 (N-(n-butyl)moranoline)

After conc. sulfuric acid was added to 160 ml of the N-(n-butyl)moranoline sugar transfer reaction solution (containing about 8 g of N-(n-butyl)moranoline prior to the sugar transfer reaction) prepared by the process of Example 11 to adjust pH to 5.2, 20 ml of the immobilized GA prepared by the process of Reference Example 3 was added to the mixture followed by reacting at 50° C. for 20 hours. The reaction mixture was filtered through a glass filter to remove the immobilized GA to give the GA reaction solution.

Example 17

Purification of glucosylmoranoline (1)

The GA reaction solution, 280 l, prepared by the process of Example 12 was passed through a column (120 l) of decoloration resin HS (manufactured by Hokuetsu Carbon Co., Ltd.) and washed with water. The liquid passed and the washing liquid were combined and the mixture was passed through a column packed with 180 l of strongly acidic ion exchange resin DIA ION SK-104 (H+). After thoroughly washing with water, the column was eluted with 1N ammonia water. After the eluate was concentrated under reduced pressure, the concentrate was passed through a column packed with 180 l of strongly basic ion exchange resin SA-11A (OH⁻) followed by elution with water. After the eluate was concentrated to about 18 l, 320 l of methanol was added to the concentrate while stirring. The mixture was stirred overnight. The resulting crystals were collected by filtration and dried to give 7.9 kg of the adduct of glucosylmoranoline with methanol.

The product was analyzed by high performance liquid chromatography under the same conditions as in Reference Example 4. The results reveal that about 3% of moranoline was present but other impurities were not significantly present.

Example 18

Purification of glucosylmoranoline (2)

The GA reaction solution, 300 l, prepared by the process of Example 13 was passed through 180 l of a column packed with strongly acidic ion exchange resin DIA ION SK-104 (H⁺). After thoroughly washing with water, the column was eluted with 1N ammonia water. The eluate was concentrated under reduced pressure to remove ammonia. The concentrate was passed through a column packed with 50 l of strongly basic ion exchange resin SA-11A (OH⁻) followed by elution with water. After the eluate was concentrated to about 20 l, 350 of methanol was added to the concentrate while stirring The mixture was stirred overnight. The resulting crystals were collected by filtration and dried to give 7.3 kg of the adduct of glucosylmoranoline with methanol.

The product was analyzed by high performance liquid chromatography under the same conditions as in Reference Example 4. The results reveal that about 0.5% of moranoline was present but other impurities were not significantly present.

Example 19

Purification of glucosyl-N-methylmoranoline

The GA reaction solution, 100 ml, prepared by the process of Example 14 was passed through 100 ml of a column packed with strongly acidic ion exchange resin DOWEX 50 x 2 (H.). After thoroughly washing with water, the column was eluted with 0.5N ammonia water. The eluate was concentrated under reduced pressure to remove ammonia. The concentrate was passed through a column packed with 100 ml of strongly basic ion exchange resin SA-11A (OH⁻) followed by elution with water. The liquid passed and the eluate were combined and the mixture was concentrated to dryness under reduced pressure. After the residue was dissolved in 50 ml of methanol, 4.8 g of p-toluenesulfonic acid (monohydrate) was added to the solution. The mixture was allowed to stand overnight at room temperature. The resulting crystals were collected by filtration and dried to give 4.4 g of the p-toluene-sulfonate of glucosyl-N-methylmoranoline.

A part of the product was taken and analyzed by high performance liquid chromatography under the same conditions as in Reference Example 4. The results reveal that about 0.5% of N-methylmoranoline was present but other impurities were not significantly present.

Example 20

Purification of glucosyl-N-(n-butyl)moranoline (1)

The GA reactionl solution, 200 ml, prepared by the process of Example 15 was passed through 200 ml of a column packed with strongly acidic ion exchange resin DOWEX 50×2 (H⁺) After thoroughly washing with water, the column was eluted with 0.5N ammonia water. The eluate was concentrated under reduced pressure to remove ammonia. The concentrate was passed through a column packed with 100 ml of strongly basic ion exchange resin SA-11A (OH⁻) followed by elution with water. The liquid passed and the eluate were combined and the mixture was concentrated to dryness under reduced pressure. After the residue was dissolved in 50 ml of methanol, 5.2 g of p-toluenesulfonic acid (monohydrate) was added to the solution. The mixture was allowed to stand overnight at room temperature. The resulting crystals were collected by filtration and dried to give 5.5 g of the p-toluene-sulfonate of glucosyl-N-(n-butyl)moranoline.

A part of the product was taken and rendered a basic fraction. The basic fraction was then analyzed by high performance liquid chromatography under the same conditions as in Reference Example 4. The results reveal that about 1.5% of N-(n-butyl)moranoline was present but other impurities were not significantly present.

Example 21

Purification of glucosyl-N-(n-butyl)moranoline (2)

The GA reaction solution, 160 ml, prepared by the process of Example 16 was passed through 200 ml of a column packed with strongly acidic ion exchange resin DOWEX 50×2 (H⁺). After thoroughly washing with water, the column was eluted with 0.5N ammonia water. The eluate was concentrated under reduced pressure to remove ammonia. The concentrate was passed through a column packed with 100 ml of strongly basic ion exchange resin SA-11A (OH⁻) followed by elution with water. The liquid passed and the eluate were combined and the mixture was concentrated to dryness under reduced pressure. After the residue was dissolved in 50 ml of methanol, 5.2 g of p-toluenesulfonic acid (monohydrate) was added to the solution. The mixture was allowed to stand overnight at room temperature. The resulting crystals were collected by filtration and dried to give 10.0 g of the p-toluene-sulfonate of glucosyl-N-(n-butyl)moranoline.

A part of the product was taken and rendered a basic fraction. The basic fraction was then analyzed by high performance liquid chromatography under the same conditions as in Reference Example 4. The results reveal that about 0.5% of N-(n-butyl)moranoline was present but other impurities were not significantly present.

Example 22

Sugar transfer reaction using ht mother liquor residue recovered upon purification of glucosylmoranoline, GA reaction and purification of moranoline Using as a raw material the residue obtained when the solvent (methanol) of the mother liquor in fractional crystallization with methanol in Example 17 was recovered and removed (recovered residues corresponding to 3 lots obtained by reacting in a manner similar to Example 7 and Example 12 and treating in a manner similar to Example 17) in Example 17, the procedures were conducted as in Example 7, Example 12 and Example 17 to give 9.0 kg of the adduct of glucosylmoranoline with methanol.

Example 23

Purification of moranoline

The methanol-adduct of glucosyl-moranoline, 1 kg, obtained by the process of Example 17 was dissolved in 1N hydrochloric acid (5 l) and the solution was reacted at 90° C. for 3 hours. The reaction solution was subjected to a column packed with 10 l of weakly basic ion exchange resin DIA ION WA-20 (OH−). After thoroughly washing with water, the liquid passed and the washing liquid were combined and the mixture was passed through a column packed with 5 l of strongly acidic ion exchange resin DIA ION SK-104 (H+). After thoroughly washing with water, the column was eluted with 1N ammonia water. The eluate was concentrated to dryness under reduced pressure to give 468 g of moranoline.

The product showed high purity without crystallization and could be used as a starting material for synthesis as it was.

Example 24

Purification of N-methylmoranoline

The p-toluenesulfonate of glucosyl-N-methyl-moranoline, 2 g, obtained by the process of Example 19 was dissolved in 1N hydrochloric acid (10 ml) and the solution was reacted at 90° C. for 3 hours. The reaction solution was subjected to a column packed with 100 ml of weakly basic ion exchange resin DIA ION WA-20 (OH−). After thoroughly washing with water, the liquid passed and the washing liquid were combined and the mixture was passed through a column packed with 50 ml of strongly acidic ion exchange resin DIA ION SK-104 (H+). After thoroughly washing with water, the column was eluted with 0.5N ammonia water. After the eluate was concentrated to dryness under reduced pressure, the residue was recrystallized from ethanol to give 590 mg of N-methylmoranoline.

Example 25

Purification of N-(n-butyl)moranoline (1)

The p-toluenesulfonate of glucosyl-N-(n-butyl)-moranoline, 3 g, obtained by the process of Example 20 was dissolved in 1N hydrochloric acid (30 ml) and the solution was reacted at 90° C. for 3 hours. The reaction solution was subjected to a column packed with 200 ml of weakly basic ion exchange resin DIA ION WA-20 (OH−). After thoroughly washing with water, the liquid passed and the washing liquid were combined and the mixture was passed through a column packed with 100 ml of strongly acidic ion exchange resin DOWEX 50 x 2 (H+). After thoroughly washing with water, the column was eluted with 0.5N ammonia water. After the eluate was concentrated to dryness under reduced pressure, the residue was recrystallized from ethanol to give 850 mg of N-(n-butyl)moranoline.

Example 26

Purification of N-(n-butyl)moranoline (2)

The p-toluenesulfonate of glucosyl-N-(n-butyl)-moranoline, 5 g, obtained by the process of Example 21 was dissolved in water and pH of the solution was adjusted to 5.2 with 1N hydrochloric acid. After the volume was adjusted to 1000 ml, 50 ml of the immobilized GA prepared by the process of Reference Example 3 was added to the solution and allowed to react at 50° C. for 24 hours. The reaction mixture was filtered through a glass filter to remove the immobilized GA. The filtrate was subjected to a column packed with 100 ml of weakly basic ion exchange resin DIA ION WA-20 (OH−). After thoroughly washing with water, the liquid passed and the washing liquid were combined and the mixture was passed through a column packed with 100 ml of strongly acidic ion exchange resin DOWEX 50 x 2 (H+). After thoroughly washing with water, the column was eluted with 0.5N ammonia water. After the eluate was concentrated to dryness under reduced pressure, the residue was recrystallized from ethanol to give 1.6 g of N-(n-butyl)moranoline.

Reference Example A

Immobilization of CGTase (1)

After 10 l of CHITOPEARL BCW-3010 manufactured by Fujibo Co., Ltd. was immersion-treated in 40 l of 0.1M acetate buffer solution (pH 6.0) containing 2.5 w/v% glutaraldehyde at room temperature for 24 hours, the mixture was thoroughly washed with ion exchange water. Then, CGTase [manufactured by Hayashibara Biochemical Research Institute, derived from Bacillus stearothermophilus] corresponding to 20 mg of protein was added per 1 ml of CHITOPEARL and acetate buffer solution (pH 6.0) was further added to the mixture in a final concentration of 0.025M to make the whole volume 30 l. The system was immersed at room temperature for 24 hours as it was. Thereafter, the mixture was thoroughly washed with ion exchange water to give immobilized CGTase. A protein adsorption amount of the resulting beads was 19.5 mg/ml (bead). Reference Example B Immobilization of CGTase (2)

CGTase derived from Bacillus Stearothermophilus was immobilized in a manner similar to Reference Example A to give a protein adsorption amount of 5 mg/ml. Reference Example C Immobilization of GA After a glucozyme NL-3 manufactured by Amano Pharmaceutical Co., Ltd. was dialyzed, it was adjusted to a protein concentration of 60 to 65 mg/ml. This was used as GA aqueous solution.

After 1 l of CHITOPEARL BCW-3010 manufactured by Fujibo Co., Ltd. was immersion-treated in 3 l of 50 mM acetate buffer solution (pH 5.0) containing 2.5 w/v% glutaraldehyde at room temperature for 24 hours, the mixture was thoroughly washed with ion exchange water. Then, GA aqueous solution corresponding to 100 mg of protein was added per 1 ml of CHITOPEARL and water was further added to the mixture to make the whole volume 3 l. The system was immersed at room temperature for 24 hours as it was. Thereafter, the mixture was thoroughly washed with ion exchange water to give immobilized GA. A protein adsorption amount of the resulting beads was 12.8 mg/ml (bead). Reference Example D Culture of moranoline-producing bacteria In an Erlenmeyer flask of 500 ml volume was charged 200 ml of medium having a composition of 2% starch, 1% soybean powders, 0.05% potassium chloride, 0.05% magnesium sulfate heptahydrate, 0.2% sodium chloride and 0.35% calcium carbonate (pH 7.2). After sterilization in a conventional manner, several platinum loops of the slant culture of Streptomyces lavendulae SEN-158 strain were inoculated on the medium and shake cultured at 27° C. for 3 days at 200 r.p.m. The resulting culture was used as a seed culture broth.

In a jar fermenter of 420 l was charged 250 l of medium having a composition of 8% starch, 3% soybean powders, 1.5% yeast extract, 0.05% potassium chloride, 0.05% magnesium sulfate heptahydrate, 0.1% sodium chloride and 0.15% calcium carbonate (pH 7.2). After sterilization in a conventional manner, 2.4 l of the seed culture broth was inoculated on the medium followed by culturing at 27° C. for 10 days at 100 r.p.m. in an aerial amount of 125 l/min. In a manner similar to Reference Example D, moranoline in the culture solution was quantitatively determined by high performance liquid chromatography. As the result, about 3500 μg/ml of moranoline was obtained.

Reference E

Partial purification of moranoline-containing culture broth

The culture broth obtained by the process of Reference Example D was passed through ultrafiltration membrane (manufactured by Kuraray Co., Ltd., UF Module; MU-6303-HG). The passed liquid was further passed through reverse osmosis membrane (manufactured by Toyobo Co., Ltd., hollow fiber; HR-5155 F1) and concentrated. The liquid which had not been passed was the partially purified product.

Reference Example F

Sugar transfer reaction of the partially purified product of moranoline-containing culture broth The partially purified product (150 l; containing about 7 kg of moranoline) obtained by treating in a manner similar to Reference Example E the culture solution (2000 l) cultured in a manner similar to Reference Example D was charged in the jar fermenter in a reaction apparatus comprising a jar fermenter of 420 l volume having connected therewith a column of 50 l volume. Furthermore, 70 kg of Amicol No. 6L wa added to the mixture and heated to dissolve the same. After pH was adjusted to 9.0 with 6N sodium hydroxide, water was added to make the whole volume 280 l. After 30 l of the immobilized CGTase prepared in Reference Example A was packed in the column, the reaction was carried out at 55° C. for o48 hours while circulating at a flow rate of 3 l/min to give the sugar transfer reaction liquid of moranoline.

Example 27

Stabilization of immobilized CGTase (sugar transfer reaction of moranoline)

The immobilized CGTase, 10 ml, obtained in Reference Example A was added to 100 ml of aqueous solution with the pH being not adjusted containing 2.5 w/v% of moranoline and 25 w/v% of Amicol No. 6L [manufactured by Nichiden Chemical Co., Ltd.] followed by rotary shaking at 55° C. After a definite period of time passed, the beads (immobilized CGTase) were filtered through a glass filter. After thoroughly washing with water, the enzyme activity of the immobilized CGTase was determined as follows. (Method for determination of enzyme activity of immobilized CGTase)

The beads (washed immobilized CGTase after a definite period of time at 55° C.), 1 ml, was added to 10 ml of aqueous solution with the pH being not adjusted containing 2.5 w/v% of moranoline and 25 w/v% of Amicol No. 6L followed by reacting at 55° C. for 24 hours The reaction liquid, 3 ml, was passed through 7 ml of strongly acidic ion exchange resin DOWEX 50W X 2 (H+). After thoroughly washing with water, elution was performed with 0.5N ammonia water. The eluate was concentrated to dryness under reduced pressure and the residue was dissolved in 3 ml of water. 10 μl of the solution was applied to and analyzed by high performance liquid chromatography to determine a concentration of the unreacted moranoline. The analytical conditions for high performance liquid chromatography were as follows: column (Nucleosil 5NH$_2$, 5 μm, 4 mm i.d. X 25 cm), developing solvent acetonitrile-water=70:30), detector (Hitachi 655A-30, RI detector), data processor (Hitachi D-2000).

Reaction progress rate (%) =

$$\frac{25 - [\text{unreacted moranoline (mg/ml)}]}{25} \times 100$$

Where the reaction progress rate was made 100 when rotary shaking started at 55° C., a relative reaction progress rate after a definite period of time passed was calculated according to the above equation. The thus obtained value was made an enzyme activity retention rate. The results are shown in Table 6. The data clearly shows that the enzyme activity of the immobilized CGTase was stabilized by the moranoline in accordance with the present invention.

TABLE 6

| Time passed (day) | | | | 0 | 14 | 21 | 28 |
|---|---|---|---|---|---|---|---|
| Activity retention rate (%) | | | | 100 | 100 | 102.7 | 101.9 |
| day | 37 | 53 | 65 | 78 | 93 | 100 | |
| % | 100.8 | 102.3 | 104.3 | 100.7 | 99.7 | 100.5 | |
| day | 119 | 140 | 163 | 178 | 198 | 210 | |
| % | 97.0 | 100.3 | 99.3 | 98.4 | 92.5 | 95.6 | |
| day | 231 | 246 | 262 | 274 | 288 | 302 | 322 |
| % | 92.5 | 93.0 | 92.3 | 92.5 | 92.7 | 92.0 | 92.7 |
| day | 339 | 353 | 366 | 413 | | | |
| % | 91.5 | 93.9 | 90.0 | 90.0 | | | |

Example 28

Stabilization of immobilized CGTase (sugar transfer continuous reaction of N-methylmoranoline)

The immobilized CGTase, 20 ml, obtained in Reference Example A was packed in a column having a diameter of 1 cm equipped with a jacket and a solution with the pH being not adjusted containing 1.5 w/v% of N-methylmoranoline and 9 w/v% of soluble starch was continuously passed through the column at 55° C. in a passing velocity of 160 ml/day to react them, whereby the reaction progress rate of the passing liquid was determined with passage of time. The reaction progress rate and activity retention rate were determined in a manner similar to Example 27. The results demonstrate that even after 140 days, almost 100% of the activity was retained

Example 29

Stabilization of immobilized CGTase (moranoline, moranoline glucose oligomer)

To 1 ml of the immobilized CGTase obtained in Reference Example B were added moranoline (2.5 w/v%) and moranoline glucose oligomer (mixture ) (5.0 w/v%) to make whole volume 10 ml. The mixture was shaken at 55° C.

The glucose oligomer of moranoline refers to the following.

After 3 w/v% of moranoline and 30 w/v% of Amicol No. 6L were dissolved in water and the whole volume was made 500 ml with the pH being not adjusted, 50 ml of the immobilized CGTase obtained in Reference Example 1 was added to the aqueous solution. After reacting at 55° C. for 48 hours, the reaction mixture was filtered through a glass filter to remove the immobilized enzyme. The filtrate was passed through a column packed with 200 ml of strongly acidic ion exchange resin DOWEX 50W x 2 (H+). The column was well washed with water, eluted with one liter of 0.5N ammonia, the eluate was evaporated in vacuo, the resulting residue was dissolved in a suitable amount of water and was subjected to a column packed with 100 ml of strongly basic ion exchange resin DIA ION SA-11A (OH). Elution was performed with water. The passed liquid and the eluate were combined and concentrated to dryness under reduced pressure. The basic fraction of the thus obtained moranoline sugar transfer reaction liquid was called glucose oligomer of moranoline.

When the enzyme activity in adjustment was made 100, the residual enzyme activity retention rate (%) is shown in Table 7. Determination of the enzyme activity, was the same as in Example 27.

It is clear that moranoline and the glucose oligomer of moranoline act to stabilize the activity of CGTase.

TABLE 7

|  | 14 Days | 28 Days | 42 Days |
|---|---|---|---|
| None | 17.7% | 12.5% | 0.0% |
| Moranoline | 81.6 | 77.8 | 70.8 |
| Glucose oligomer of moranoline | 100.0 | 99.0 | 95.7 |

Example 30

Stabilization of immobilized CGTase (N-substituted moranoline, N-substituted glucosylmoranoline)

To 1 ml of the immobilized CGTase obtained in Reference A were added N-substituted moranoline (0.5 w/v%) and N-substituted glucosylmoranoline (0.5 w/v%) to make whole volume 10 ml. After the mixture was shaken at 55° C. for 14 days, the residual enzyme activity rate when the initial enzyme activity was made 100 is shown in Table 8 Determination of the enzyme activity was performed as in Example 27.

It is clear that the compound of the present invention shows a good stabilizing action.

TABLE 8

| Residual enzyme activity rate (%) | Activity Rate (%) |
|---|---|
| Water | 15.0% |
| N-Butylmoranoline | 68.5 |
| N-Phenylethylmoranoline | 75.0 |
| N-Phenoxyethylmoranoline | 37.1 |
| Glucosyl-N-butylmoranoline | 100.0 |
| Glucosyl-N-phenylethylmoranoline | 88.4 |
| Glucosyl-N-phenoxyethylmoranoline | 74.0 |

Example 31

Stabilization of immobilized GA (sugar transfer reaction liquid of moranoline)

The pH of the reaction solution containing the unreacted moranoline, the unreacted Amicol No. 6L and oligoglucosylmoranoline prepared in Reference Example F was adjusted to 5.2 using sulfuric acid. The reaction solution was continuously passed at 50° C. through a column having a diameter of 1 cm equipped with a jacket, which had been packed with 20 ml of the immobilized GA obtained in Reference Example C, in a passing velocity of 480 ml/day to react them. After reacting for a definite period of time, the immobilized GA in the column was taken out and the enzyme activity was determined by the following method, whereby the activity retention rate (stability) when the enzyme activity at the initiation of the reaction was made 100% was determined. The results are shown in Table 9.

Method for determination of enzyme activity of immobilized GA

A definite amount (wet weight, 30 to 80 mg) of the immobilized GA was taken on a glass filter and gently sucked to filter the water off. Thereafter, the immobilized GA on the glass filter was put on a lens paper to remove an excess of water. Then, the residue was charged in a sample bottle with a stopper to determine wet weight of the immobilized GA. Next, the immobilized GA was added to 10 ml of 5% maltose solution (0.05M acetate buffer solution, pH 4.6) followed by incubation at 37° C. for 20 minutes. 100 μl of the reaction solution was added to 0.05N sodium hydroxide to terminate the reaction.

Using 10 μl of the reaction terminated solution, glucose was quantitatively determined. The quantitative determination of glucose was performed using DIA COLOR GC (manufactured by Ono Pharmaceutical Co., Ltd.).

The activity was defined as follows. The activity of enzyme which produces 1 μM of glucose for one minute is made one unit. For blank, 0.05N sodium hydroxide mixed with substrate in an equivolume instead of the reaction solution was used.

In this case, the activity of the immobilized GA showed 5.56 x $OD_{SA}/OD_{STD}$/wet weight of the immobilized GA, wherein $OD_{SA}$ represents absorbancy of sample (immobilized GA) at 500 nm and $OD_{STD}$ represents absorbancy of 1 mg/ml glucose aqueous solution at 500 nm. In Table 9, the value of the activity retention rate varies but this is due to error in measurement. The stabilizing action of the compound of the present invention on immobilized GA is clearly demonstrated.

TABLE 9

| Time passed (day) | 0 | 7 | 14 | 21 | 28 |
|---|---|---|---|---|---|
| Activity retention rate (%) | 100 | 96 | 82 | 88 | 80 |
| day | 35 | 42 | 49 | 56 | 63 | 70 |
| % | 92 | 85 | 104 | 111 | 96 | 97 |
| day | 77 | 84 | 91 | 98 | 105 | 112 |
| % | 90 | 79 | 86 | 82 | 75 | 76 |
| day | 119 | 126 | 133 | 140 | 147 | 154 |
| % | 76 | 76 | 79 | 76 | 86 | 75 |
| day | 161 | 168 | 175 |
| % | 77 | 77 | 80 |

Example 32

Stabilization of immobilized GA (sugar transfer reaction liquid of moranoline

In a manner similar to Example 31, the experiment was performed at 40° C. The results are shown in Table 10.

TABLE 10

| Time passed (day) | 0 | 7 | 14 | 21 | 28 |
|---|---|---|---|---|---|
| Activity retention rate (%) | 100 | 96 | 86 | 92 | 77 |
| day | 35 | 42 | 49 | 56 | 63 | 70 |
| % | 96 | 96 | 127 | 130 | 108 | 97 |
| day | 77 | 84 | 91 | 98 | 105 | 112 |
| % | 90 | 86 | 107 | 89 | 86 | 83 |
| day | 119 | 126 | 133 | 140 | 147 | 154 |
| % | 90 | 97 | 89 | 92 | 96 | 96 |
| day | 161 | 168 | 175 |
| % | 97 | 83 | 90 |

Example 33

Stabilization of GA (aqueous solution) (moranoline, N-methylmoranoline)

Since moranoline and N-methylmoranoline inhibit the enzyme activity of glucoamylase, the stabilizing effect to glucoamylase in a solution state was examined as follows. As the enzyme, Rhizopus niveus-derived reagent glucoamylase manufactured by Biochemical Industry Co., Ltd. was used.

After 5 mg of the enzyme was dissolved in 1 ml of 0.1M acetate buffer solution (pH 5.0), moranoline and N-methylmoranoline were dissolved in the solution in a concentration of 6000 µg/ml. The solution was charged in a test tube with a screw stopper followed by incubation at 50° C. Each enzyme solution was diluted with 0.1M acetate buffer solution (pH 5.0) to 100-fold and 100 µl of the dilution was taken. After 400 µl of 5% maltose solution (0.05M acetate buffer solution, pH 4.6) was added thereto, the mixture was reacted at 40° C. for 20 minutes. 100 µl of the reaction solution was taken and 100 µl of 0.05N sodium hydroxide was added thereto to terminate the reaction. Further, 100 µl of the reaction solution was taken and 3.0 ml of reagent DIA COLOR GC for measuring glucose was added thereto. The mixture was settled at 37° C. for 30 minutes to form a color. Thereafter, the system was ice cooled and absorbancy was measured at 500 nm to determine the glucose amount. The amount of glucose produced was made enzyme activity in the co-presence of inhibitor. When the initial enzyme activity (amount of glucose produced) was made 100, relative enzyme activity was determined. The results are shown in FIG. 2. The enzyme stabilizing activity of the compound of the present invention is clearly seen.

Example 34

Stabilization of immobilized GA (moranoline, N-alkylmoranoline

To 5 ml of the immobilized GA prepared in Reference Example C was added 10 ml of 0.1M acetate buffer solution (pH 5.0). The mixture was charged in an air-tight bottle. In this case, moranoline and N-alkylmoranoline were dissolved therein in a concentration of 100 mM followed by incubation at 55° C. The residual enzyme activity was measured by the method described in Example 31. The results are shown in FIG. 3. The enzyme stabilizing activity of the compound of the present invention is clearly seen.

Example 35

Stabilization of β-glucosidase by moranoline and N-methylmoranoline

The stabilizing effect of moranoline and N-methylmoranoline on β-glucosidase was examined. Test samples were (1) 1 ml of 0.2M buffer solution of β-glucosidase (300 µg/ml) alone, (2) 1 ml of 0.2M buffer solution of β-glucosidase (300 µg/ml) supplemented with 6 mg/ml of moranoline hydrochloride and, (3) 1 ml of 0.2M buffer solution of β-glucosidase (300 µg/ml) supplemented with 6 mg/ml of N-methylmoranoline hydrochloride. These test samples were kept at 60° C. and the residual enzyme activity was measured with passage of time.

For determination of the enzyme activity, there was used a method measuring absorbancy at 400 nm using p-nitro-β-D-glucoside as a substrate.

That is, 200 µl of 0.014M p-nitrophenyl-β-D-glucoside, 200 µl of the enzyme solution taken from each sample for sampling with passage of time which was appropriately diluted, and 600 µl of 0.2M acetate buffer solution (pH 4.5) were reacted at 30° C. for 15 minutes. After 2 ml of 0.1M disodium carbonate was added thereto to terminate the reaction, a color was formed and the color was measured at 400 nm. When absorbancy at the initiation of the reaction was made 100, relative absorbancy in each time was defined to be residual activity.

The results are shown in FIG. 4. The stabilizing effect of moranoline and N-methylmoranoline is clearly seen.

Example 36

Stabilized immobilized CGTase

A part of the immobilized CGTase with which the sugar transfer reaction had been carried out by the method of Reference Example F was taken and thoroughly washed with water. To 5 ml of the immobilized CGTase was added 10 ml of 0.1M acetate buffer solution (pH 6.0). The mixture was placed in an air-tight bottle. After keeping at 60° C., the residual enzyme activity was measured with passage of time.

On the other hand, the immobilized CGTase prepared in Reference Example A was also stored in a similar manner and the residual enzyme activity was determined. For determining the enzyme activity, the method described in literature (Y. Ezure; Agric. Biol. Chem., 49, 2159 (1985) was used. As the result, the immobilized CGTase prepared in Reference Example A retained the CGTase activity of only about 28% but the immobilized enzyme which had been thoroughly washed with water after the sugar transfer reaction retained the enzyme activity of about 91%.

Example 37

Stabilization of α-amylase (glucose oligomer of moranoline

After α-amylase (manufactured by Seikagaku Kogyo Co., Ltd.) was dissolved in 0.2M acetate buffer solution (pH 6.0) in a concentration of 200 µg/ml, glucose oligomer of moranoline was added to the solution in a concentration of 6000 µg/ml. The mixture was incubated at 60° C. and the residual activity was measured with passage of time. The residual activity of o-amylase was determined reaction solution obtained by reacting at 40 C for 15 minutes in 0.2M acetate buffer solution (pH 5.5) using as substrate 1% soluble starch by the 3,5-dinitrosalicylic acid method (Experimental Textbook of Agricultural Chemistry, Kyoto University, 9th Print, volume 2, page 619). The relationship between the residual rate (%) to the initial enzyme activity and time is shown in FIG. 5. For control, a sample added with no glucose oligomer of moranoline was used.

The stabilizing action of the glucose oligomer of moranoline in accordance with the present invention on α-amylase is clearly demonstrated.

Example 38

Stabilization of β-amylase (moranoline)

After α-amylase of soybean origin was dissolved in 0.02M acetate buffer solution (pH 4.8) in a concentration of 500 µg/ml, moranoline was added to the solution in a concentration of 6000 µg/ml. The mixture was incubated at 65° C. and the residual activity was measured with passage of time. For control, a sample added with no moranoline was used.

The activity of β-amylase was determined by the 3,5-dinitrosalicylic acid method of Example 37. The results are shown in FIG. 6.

The stabilizing action of the moranoline in accordance with the present invention on β-amylase is clearly demonstrated.

Symbols o, ● and Δ show control, 6 mg/ml of moranoline and 6 mg/ml of N-methylmoranoline, respectively.

Figure 1:
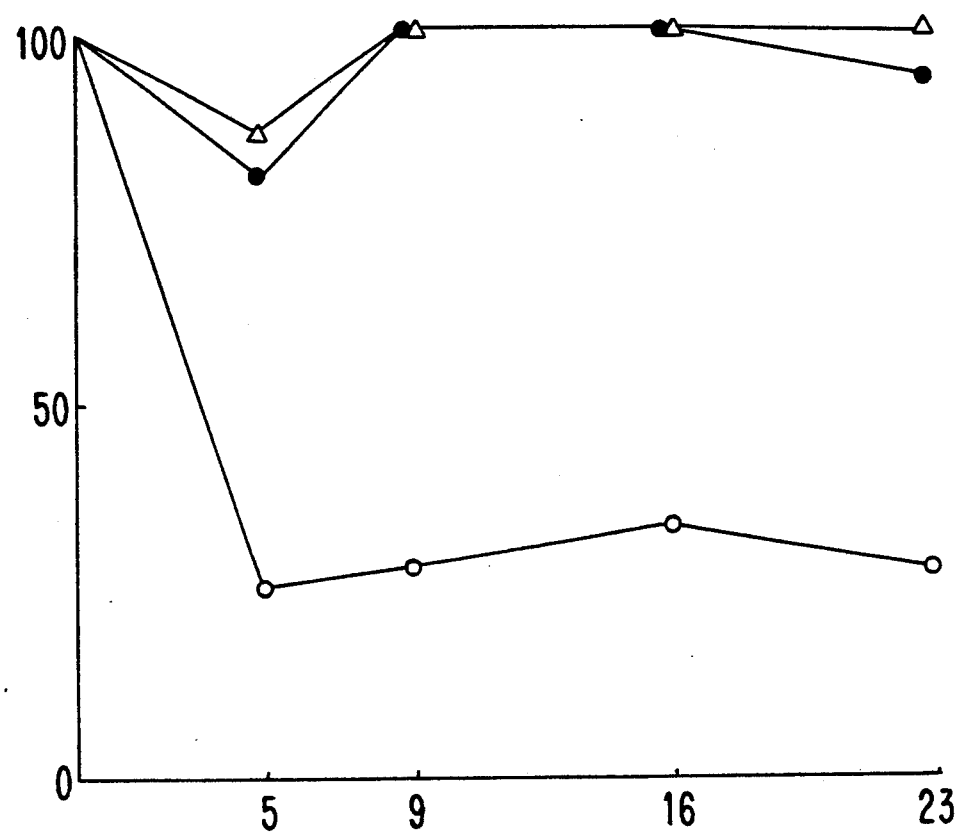
FIG. 1 illustratively shows the stabilizing action with GA in Reference Example 10, wherein the abscissa indicates time (day) and the ordinate indicates relative enzyme activity.
Figure 2:
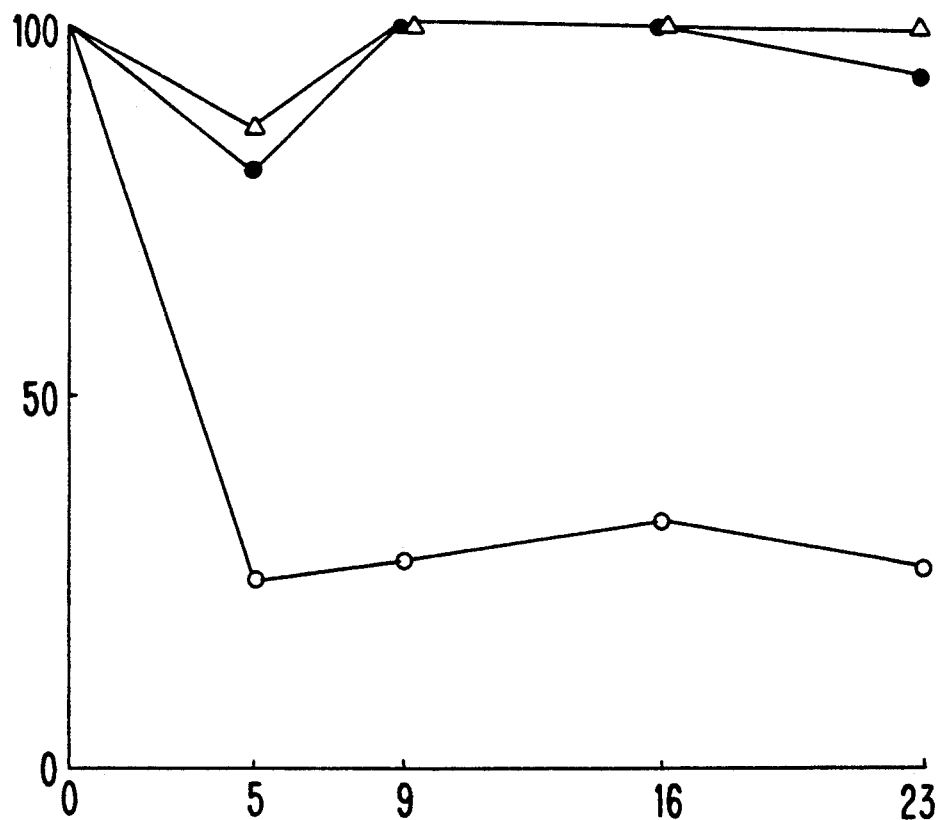

FIG. 2 shows the results of Example 33, wherein the ordinate indicates the residual rate of activity (%) and the abscissa indicates time (day).

Symbols o, ● and Δ show control, moranoline and N-methylmoranoline, respectively.

Figure 3:
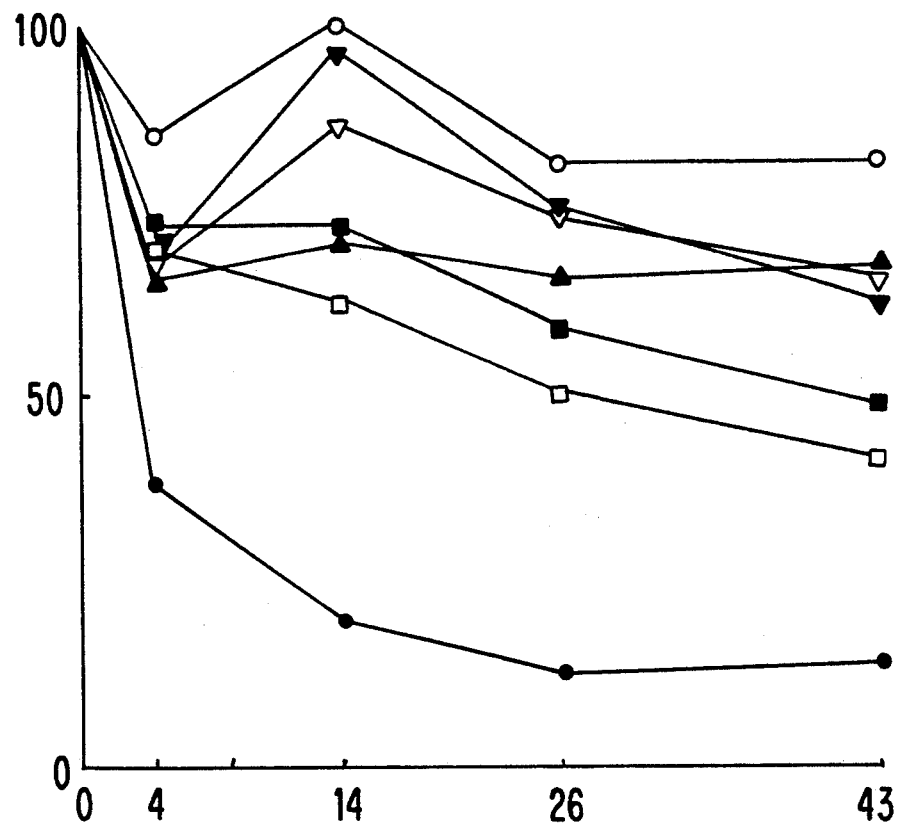

FIG. 3 shows the results of Example 34, wherein the ordinate indicates the residual rate of activity (%) and the abscissa indicates time (day).

Symbols o, ● and ▲, ■, □, ▼ and ∇ show moranoline, control, N-methylmoranoline, N-ethylmoranoline, N-(n-propyl)moranoline, N-(n-butyl)moranoline and N-(n-amyl)moranoline, respectively.

Figure 4:
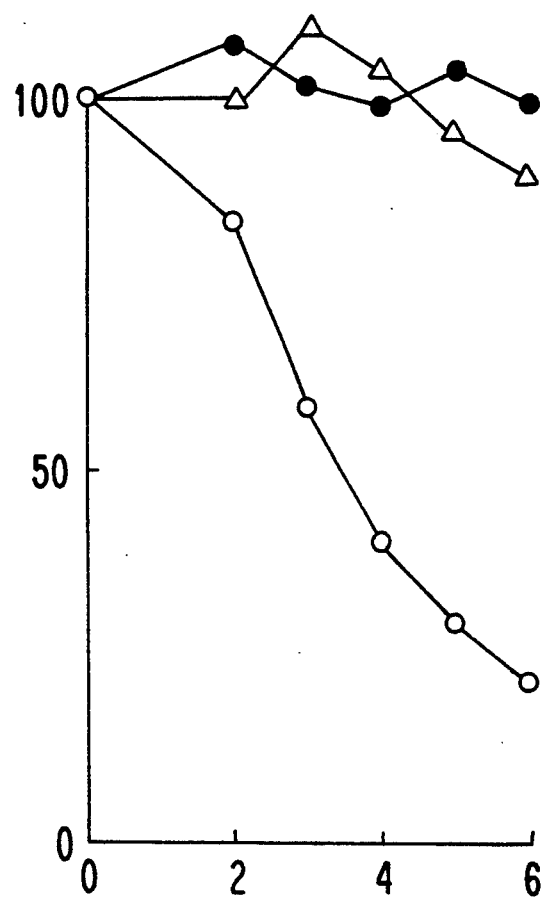

FIG. 4 shows the results of Example 35, wherein the ordinate indicates the residual rate of activity (%) and the abscissa indicates time (hour).

Symbols o, ● and Δ show control, moranoline and N-methylmoranoline, respectively.

Figure 5:
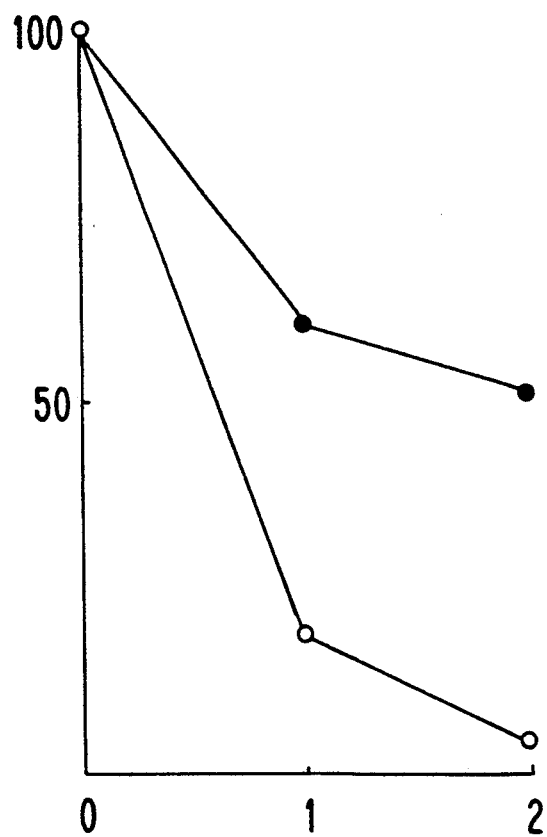

FIG. 5 shows the results of Example 37, wherein the ordinate indicates the residual rate of activity (%) and the abscissa indicates time (hour).

Symbols o and ● show control and glucose oligomer of moranoline, respectively.

Figure 6:
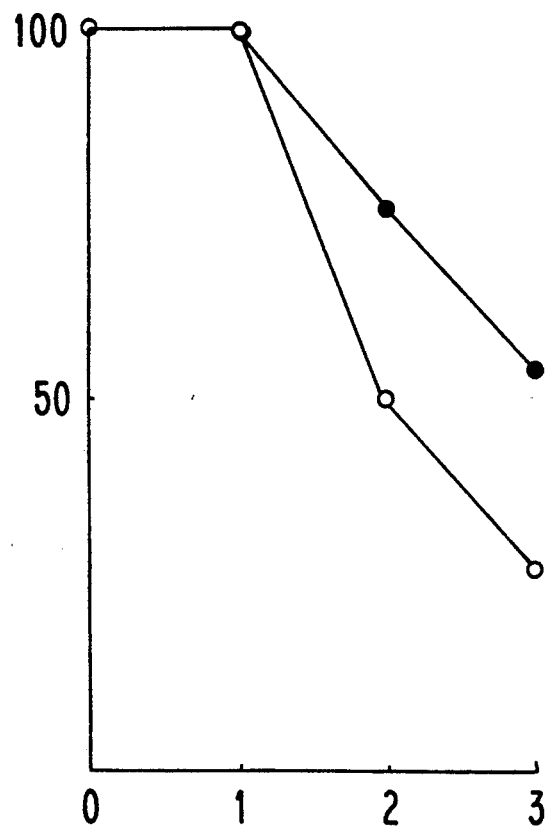

FIG. 6 shows the results of Example 38, wherein the ordinate indicates the residual rate of activity (%) and the abscissa indicates time (hour).

Symbols o and ● show control and glucose oligomer of moranoline, respectively.

What is claimed is:

1. A stabilizing agent for an enzyme which comprises an enzyme stabilizing amount of an N-substituted moranoline derivative of the formula (III):

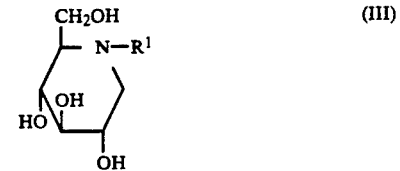

wherein $R^1$ is phenyl lower alkynyl, phenoxy lower alkenyl or phenoxy lower alkynyl, wherein the phenyl moiety is unsubstituted or substituted, or a glucose oligomer thereof.

2. A stabilizing agent according to claim 1 wherein the phenyl moiety is unsubstituted.

3. A stabilizing agent according to claim 1 wherein $R^1$ is phenyl lower alkynyl.

4. A stabilizing agent according to claim 1 wherein $R^1$ is phenoxy lower alkenyl.

5. A stabilizing agent according to claim 1 wherein $R^1$ is phenoxy lower alkynyl.

6. A stabilizing agent according to claim 1 wherein the N-substituted moranoline derivative is a glucose oligomer thereof of the formula (IV):

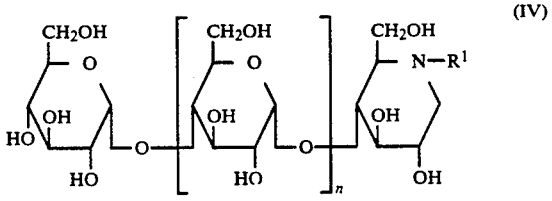

wherein $R^1$ is lower alkyl, phenyl lower alkyl, phenyl lower alkylenyl, phenyl lower alkynyl, phenoxy lower alkyl, phenoxy lower alkenyl or phenoxy lower alkynyl and n is a integer from 1 to 24.

* * * * *